United States Patent
Okada et al.

(10) Patent No.: US 7,433,445 B2
(45) Date of Patent: Oct. 7, 2008

(54) APPARATUS FOR AND METHOD OF CAPTURING RADIATION IMAGE

(75) Inventors: Naoyuki Okada, Minami-ashigara (JP); Tomonari Sendai, Minami-ashigara (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 11/714,159

(22) Filed: Mar. 6, 2007

(65) Prior Publication Data
US 2007/0211859 A1   Sep. 13, 2007

(30) Foreign Application Priority Data
Mar. 7, 2006   (JP)   ............ 2006-061030

(51) Int. Cl.
H05G 1/42   (2006.01)
(52) U.S. Cl. .......................... 378/97; 378/37
(58) Field of Classification Search ............ 378/37, 378/96, 97, 108, 101
See application file for complete search history.

(56) References Cited

U.S. PATENT DOCUMENTS 5,396,532 A    3/1995   Aichinger et al.
2002/0191741 A1*  12/2002  Brendler et al. ............ 378/96

FOREIGN PATENT DOCUMENTS

JP   2607256 Y2   3/2001
JP   2004-209152 A   7/2004

* cited by examiner

Primary Examiner—Courtney Thomas
(74) Attorney, Agent, or Firm—Sughrue Mion, PLLC (57) ABSTRACT

A radiation application time upper limit calculator calculates a radiation application time upper limit based on a subject thickness, as measured by a subject thickness measuring unit. While an X-ray tube is controlled according to exposure conditions that have been set in order to apply a radiation X to a breast to capture a radiation image thereof, an X-ray tube controller compares the applied radiation time with the radiation application time upper limit. If the applied radiation time exceeds the radiation application time upper limit, then application of radiation to the subject is interrupted, so as to prevent an inappropriate radiation dosage from being applied to an X-ray detector.

27 Claims, 6 Drawing Sheets

APPARATUS FOR AND METHOD OF CAPTURING RADIATION IMAGE

BACKGROUND OF THE INVENTION

1. Field of the Invention

The present invention relates to an apparatus for and a method of capturing a radiation image by emitting radiation from a radiation source and applying the emitted radiation to a subject.

2. Description of the Related Art

In the medical field, for example, it has been customary to apply radiation to a subject and to detect the amount of radiation that has passed through the subject with a radiation detector, or to guide the radiation that has passed through the subject directly to an X-ray film or the like, thereby forming a radiation image of the subject for diagnostic purposes.

For obtaining a radiation image suitable for image interpretation and diagnosis, a tube voltage, a tube current, and a radiation application time are established as appropriate exposure conditions, in view of the body region to be imaged and other characteristics of the radiation source.

According to the conventional X-ray image capturing apparatus disclosed in Japanese Laid-Open Patent Publication No. 2004-209152, parameters such as thickness data produced when the thickness of a subject is measured, the tube voltage of the radiation source, the distance from the radiation source to the radiation detector, the sensitivity of the radiation source, and the absorption rate at which the subject absorbs radiation (radiation attenuation coefficient) are established. Then, a tube current and a radiation application time are calculated using the established parameters.

Ordinary radiation image capturing apparatus are associated with a device (exposure control device) for detecting a radiation dosage that has passed through a subject, or a radiation dosage that is applied in the vicinity of the subject, when a radiation image of the subject is captured under the exposure conditions referred to above, whereupon application of the radiation is automatically stopped when the detected radiation dosage reaches a required radiation dosage that has been determined from the exposure conditions (see Japanese Utility Model Registration No. 2607256). The exposure control device allows the subject to be irradiated with an adequate amount of radiation for capturing a suitable radiation image of the subject, while also preventing the subject from being irradiated excessively.

When a radiation dosage applied to a subject is controlled by such an exposure control device, if an implant is embedded in the breast of a subject, for example, then the dose of radiation that passes through the subject becomes smaller than normal. Therefore, even if the radiation dose applied to the subject is excessively high, the radiation dose may possibly be detected as a radiation dosage that is lower than the required radiation dosage. Furthermore, an excessive radiation dosage cannot be detected in the event of a failure of the exposure control device, including failure of the radiation detector therein.

SUMMARY OF THE INVENTION

It is a general object of the present invention to provide an apparatus for and a method of capturing a radiation image while reliably preventing a subject from being excessively irradiated with radiation.

A major object of the present invention is to provide an apparatus for and a method of capturing a radiation image while preventing a subject from being irradiated with an excessive amount of radiation due to an operation failure of the radiation detector that detects the radiation dose.

Another object of the present invention is to provide an apparatus for and a method of capturing a radiation image while preventing a subject from being irradiated with an excessive amount of radiation due to a state of the subject.

Still another object of the present invention is to provide an apparatus for and a method of capturing a radiation image while preventing a subject from being excessively irradiated with radiation before radiation image information of the subject is captured.

Yet another object of the present invention is to provide an apparatus for and a method of capturing a radiation image, while providing the ability to announce a malfunction of the apparatus.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
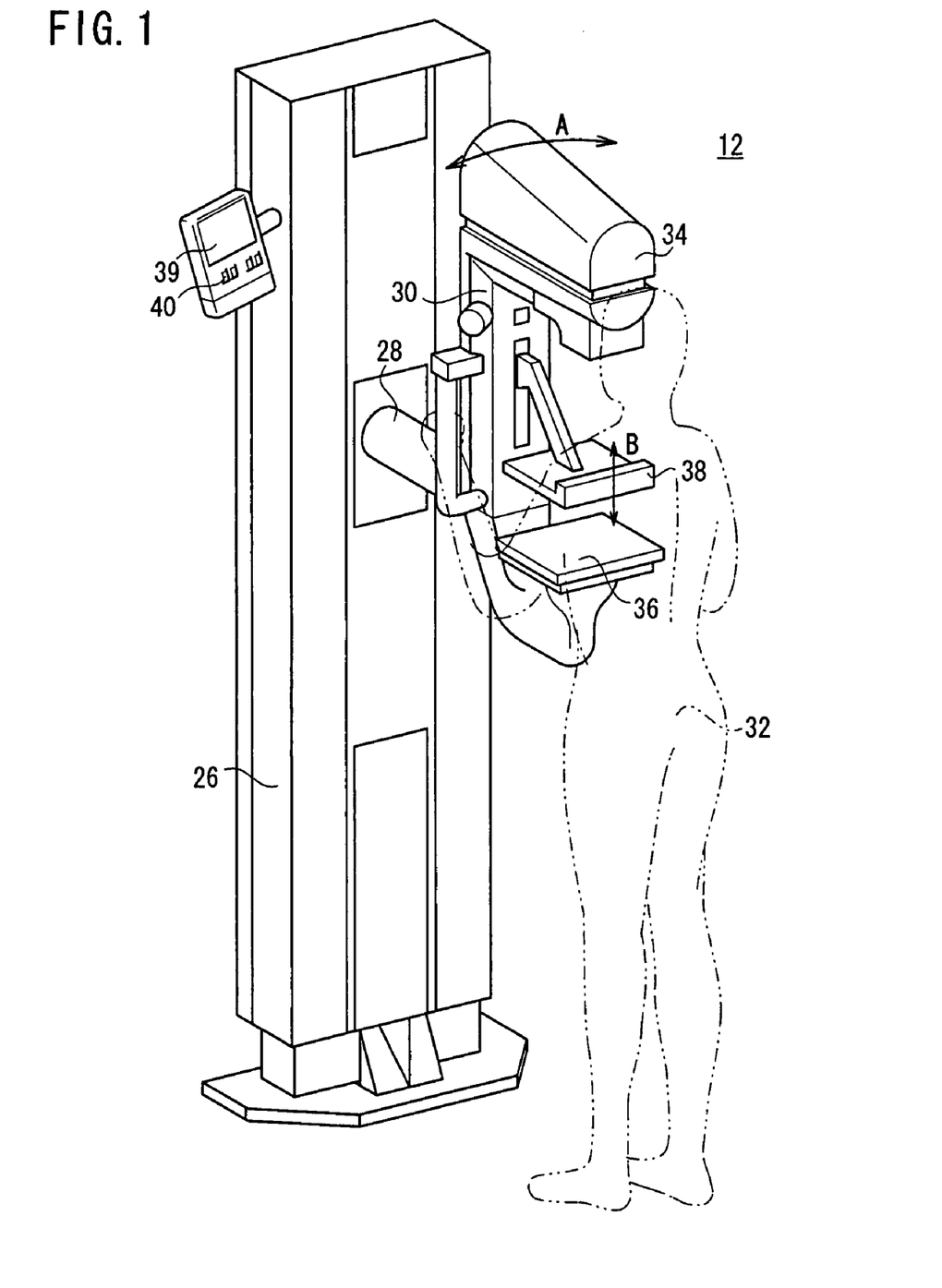
FIG. 1 is a perspective view of a mammographic system according to an embodiment of the present invention.

FIG. 1 shows in perspective a mammographic system 12 to which an apparatus for and method of capturing a radiation image according to an embodiment of the present invention are applied.

As shown in FIG. 1, the mammographic system 12 has an upstanding base 26, a vertical arm 30 fixed to a horizontal swing shaft 28 disposed substantially centrally on the base 26, a radiation source housing unit 34 storing a radiation source for applying a radiation to a subject 32 and which is fixed to an upper end of the arm 30, an image capturing base 36 housing a solid-state detector for detecting radiation that has passed through the subject 32 and which is fixed to a lower end of the arm 30, and a presser plate 38 for pressing and holding the subject's breast against the image capturing base 36.

When the arm 30, to which the radiation source housing unit 34 and the image capturing base 36 are secured, is angularly moved about the swing shaft 28 in a direction indicated by the arrow A, an image capturing direction with respect to the breast of the subject 32 can be adjusted. The presser plate 38 is connected to the arm 30 and is disposed between the radiation source housing unit 34 and the image capturing base 36. The presser plate 38 is vertically displaceable along the arm 30 in a direction indicated by the arrow B.

To the base 26, there are connected a control panel 40 for entering image capturing information including ID information of the subject 32, an image capturing region of the subject 32, a tube voltage, a target type, etc., and a display panel 39 for displaying the entered image capturing information as well as alarm information in case the application of radiation is forcibly interrupted. The display panel 39 and the control panel 40 may be mounted on a console (not shown) connected to the mammographic system 12, rather than being mounted on the mammographic system 12 itself.

Figure 2:
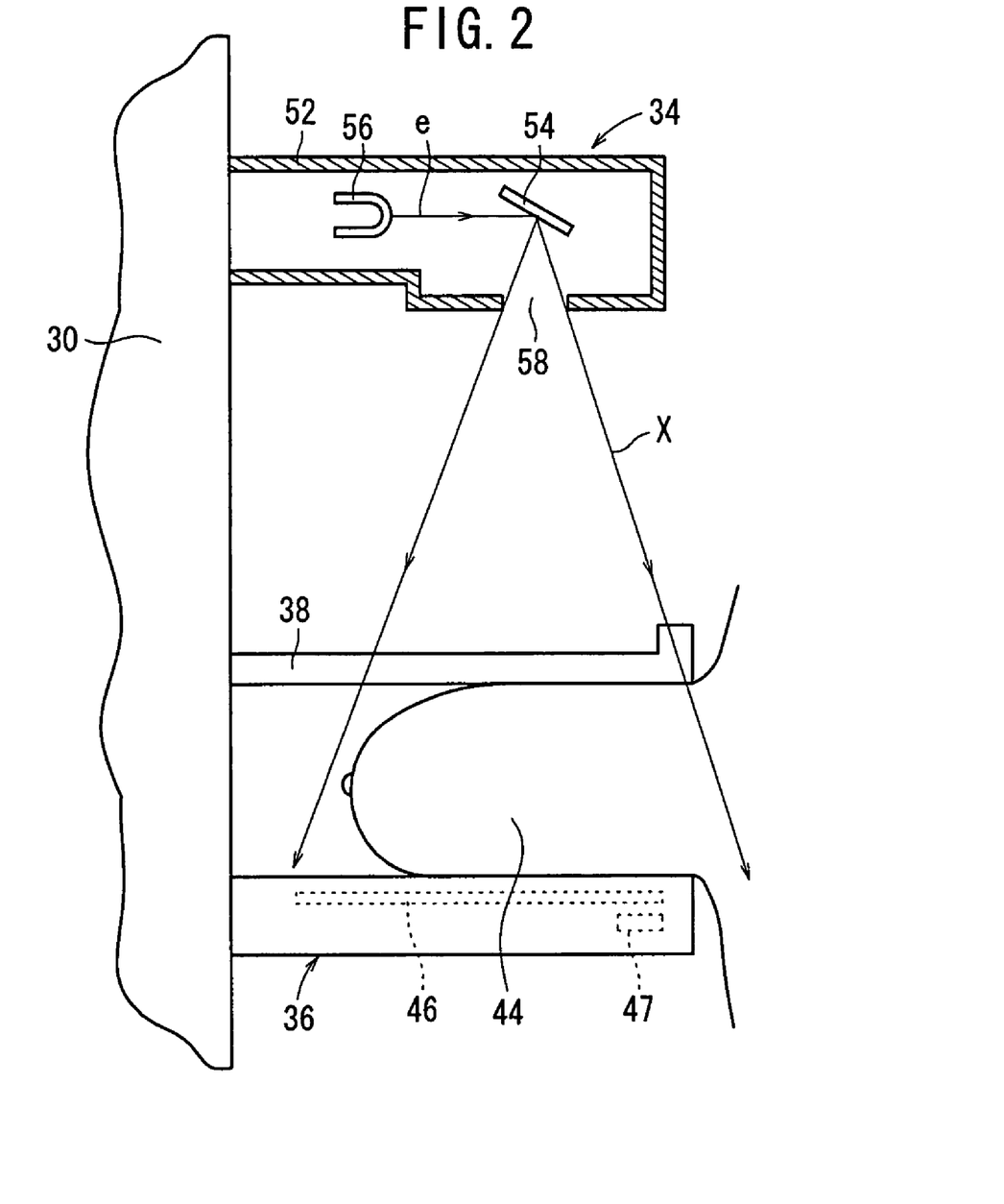
FIG. 2 is a fragmentary vertical elevational view, partly in cross section, showing internal structural details of a radiation source housing unit of the mammographic system according to the embodiment of the present invention.

FIG. 2 shows internal structural details of the radiation source housing unit 34.

As shown in FIG. 2, the radiation source housing unit 34 has a target 54 serving as a radiation source made of molybdenum, tungsten, or the like, which is placed in a housing 52, and a cathode 56 for emitting an electron beam "e" to the target 54. The housing 52 has an opening 58 defined in a lower wall through which radiation X, which is generated when the electron beam "e" emitted from the cathode 56 bombards the target 54, passes toward a breast 44 of the subject 32 that is to be imaged within a predetermined exposure field. The housing 52 is made of a heavy metal for preventing radiation from leaking outside of the housing 52. A filter, not shown, for reducing the dose of radiation X is mounted in the opening 58.

Figure 3:
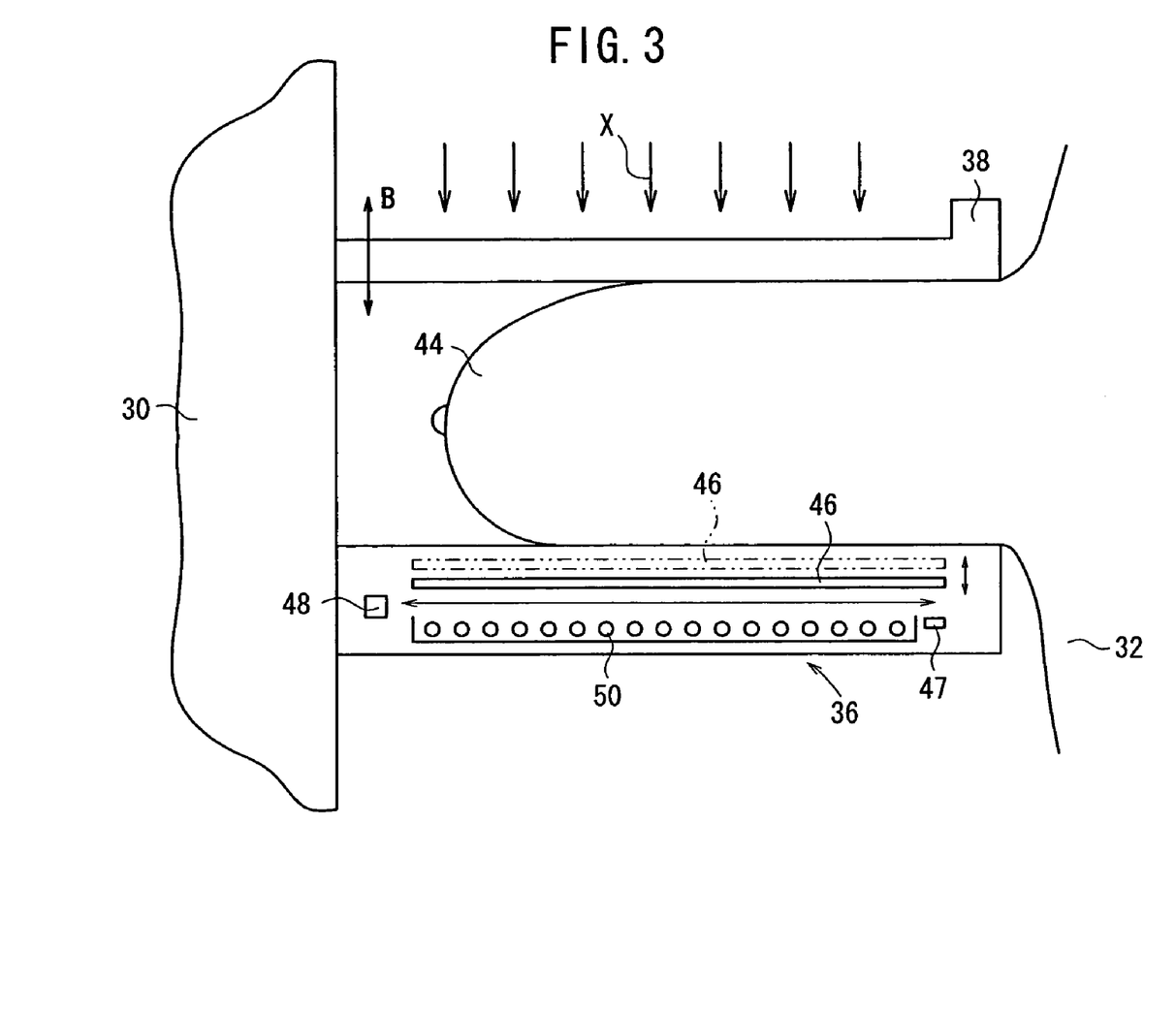
FIG. 3 is a fragmentary vertical elevational view, partly in cross section, showing internal structural details of an image capturing base of the mammographic system according to the embodiment of the present invention.

FIG. 3 shows internal structural details of the image capturing base 36 of the mammographic system 12. In FIG. 3, the breast 44 of the subject 32 is shown as being placed between the image capturing base 36 and the presser plate 38.

The image capturing base 36 houses therein an X-ray detector 46 for detecting the radiation X that is emitted from the target 54 of the radiation source housing unit 34 through the opening 58, an exposure control sensor 47 (radiation dose detecting means) for detecting the dose of radiation X that is applied to the breast 44 for performing exposure control, a reading light source 48 for applying a reading light to the X-ray detector 46 so as to read information of the radiation X that is detected by the X-ray detector 46, and an erasing light source 50 for applying an erasing light to the X-ray detector 46 in order to remove unwanted electric charges accumulated within the X-ray detector 46. A Bucky unit, not shown, for removing dispersed radiation is disposed between the X-ray detector 46 and the breast 44.

The X-ray detector 46 comprises a direct-conversion, light-reading radiation solid-state detector. The X-ray detector 46 stores information of the radiation X that has passed through the breast 44 as an electrostatic image, and when the X-ray detector 46 is scanned by reading light applied from the reading light source 48, generates a current depending on the electrostatic image. For acquiring a radiation image, the X-ray detector 46 is moved to a position near the breast 44, and when unwanted electric charges are to be removed from the X-ray detector 46, the X-ray detector 46 is moved to a position near the erasing light source 50.

More specifically, the X-ray detector 46 comprises a laminated assembly made up of a first electrically conductive layer disposed on a glass substrate for passing the radiation X therethrough, a recording photoconductive layer for generating electric charges upon exposure to the radiation X, a charge transport layer which acts substantially as an electric insulator with respect to latent image polarity electric charges developed in the first electrically conductive layer, and further which acts substantially as an electric conductor with respect to transport polarity charges, which are of a polarity opposite to the latent image polarity electric charges, a reading photoconductive layer for generating electric charges and which becomes electrically conductive upon exposure to the reading light, and a second electrically conductive layer which is permeable to the radiation X. An electric energy storage region is provided within an interface between the recording photoconductive layer and the charge transport layer.

The first electrically conductive layer and the second electrically conductive layer each provides an electrode. The electrode provided by the first electrically conductive layer comprises a two-dimensional flat electrode. The electrode provided by the second electrically conductive layer comprises a plurality of linear electrodes, which are spaced at a predetermined pixel pitch, for detecting the information of the radiation X that is to be recorded as an image signal. The linear electrodes are arranged in an array along a main scanning direction, and extend in an auxiliary scanning direction perpendicular to the main scanning direction.

The reading light source 48 has, for example, a line light source comprising a linear array of LED chips and an optical system for applying a line of reading light emitted from the line light source to the X-ray detector 46. The linear array of LED chips extends perpendicularly to the direction in which the linear electrodes of the second electrically conductive layer of the X-ray detector 46 extend. The line light source moves along the direction in which the linear electrodes extend so as to expose and scan the entire surface of the X-ray detector 46.

The erasing light source 50 should preferably comprise a light source, which can emit and quench light within a short period of time and which has very short persistence. For example, the erasing light source 50 may comprise a plurality of external-electrode rare-gas fluorescent lamps, extending along the direction of the array of LED chips of the reading light source 48 and arranged in an array perpendicular to the direction of the array of LED chips of the reading light source 48.

The exposure control sensor 47 detects the radiation X that has passed through the subject 32 and the X-ray detector 46 as a radiation dosage applied to the subject 32. The exposure control sensor 47 comprises a photosensor, for example.

Figure 4:
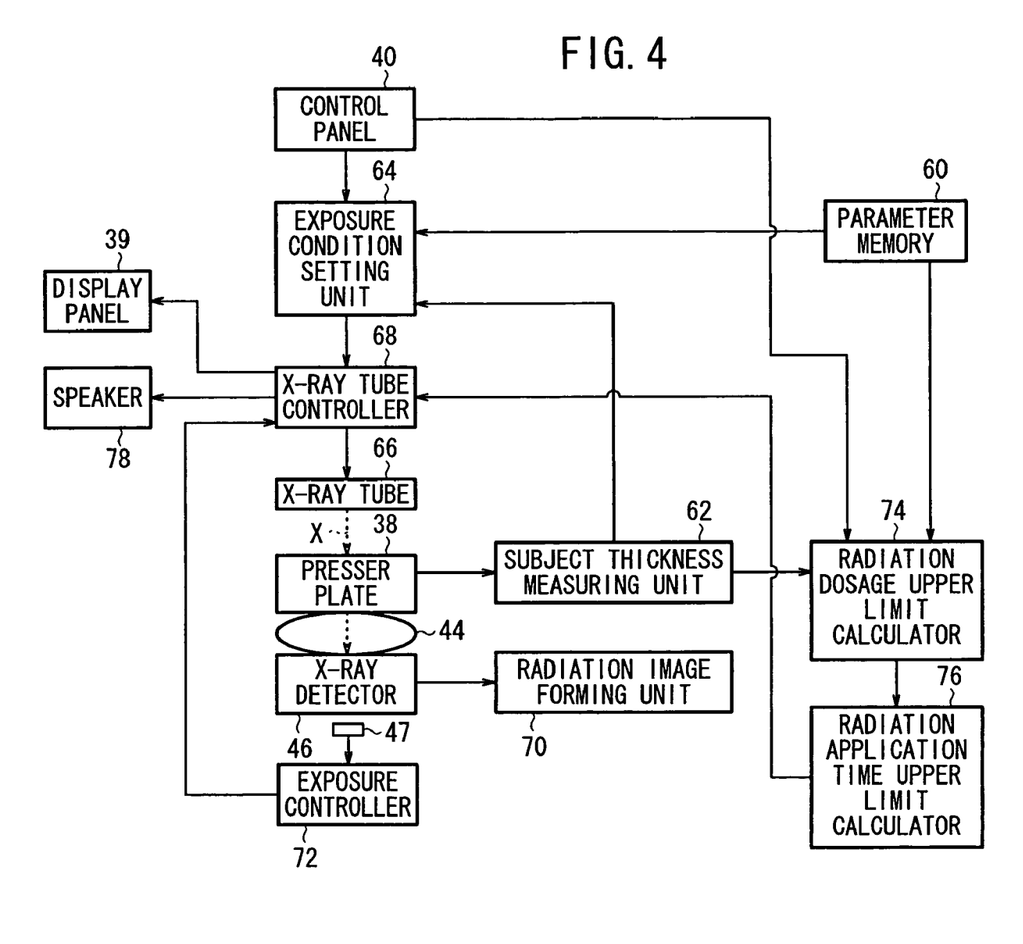
FIG. 4 is a block diagram of a control circuit of the mammographic system according to the embodiment of the present invention.

FIG. 4 shows in block form a control circuit of the mammographic system 1.2.

As shown in FIG. 4, the mammographic system 12 includes a parameter memory 60 for storing various parameters such as the absorption rates of different regions to be imaged at which the subject 32 absorbs the radiation X, the absorption rates at which the presser plate 38 and the Bucky unit absorb the radiation X, the sensitivity of the X-ray detector 46, an index that depends on the atomic number of the target 54, the attenuation characteristics of the radiation X depending on the distance between the target 54 and the X-ray detector 46, etc. The mammographic system 12 further includes a subject thickness measuring unit 62 for measuring from positional information of the presser plate 38 a subject thickness, i.e., the thickness of a region to be imaged, and an exposure condition setting unit 64 (required radiation dosage setting means) for setting exposure conditions including a tube current, a radiation application time, a radiation dosage required to capture a radiation image, etc., using image capturing information representing the region to be imaged of the subject 32, a tube voltage, the target 54 type that have been entered from the control panel 40, parameters read from the parameter memory 60, and data of the subject thickness supplied from the subject thickness measuring unit 62. In addition, the mammographic system 12 includes an X-ray tube controller 68 (radiation source control means) for controlling an X-ray tube 66, which comprises the cathode 56 and the target 54 of the radiation source housing unit 34, according to exposure conditions set by the exposure condition setting unit 64, a radiation image forming unit 70 for forming a radiation image of the breast 44 based on information of the radiation X detected by the X-ray detector 46, and an exposure controller 72 for integrating the dosage of the radiation X detected by the exposure control sensor 47 and supplying the integrated radiation dosage back to the X-ray tube controller 68 through a feedback loop for automatic exposure control.

The mammographic system 12 also has a radiation dosage upper limit calculator 74 (radiation dosage upper limit setting means) for calculating an upper limit for the dosage of the radiation X to be applied to the subject 32, from information representing the image capturing information entered from the control panel 40, parameters read from the parameter memory 60, and the subject thickness as measured by the subject thickness measuring unit 62. Further, the mammographic system 12 also has a radiation application time upper limit calculator 76 (radiation application time upper limit setting means) for calculating a radiation application time upper limit, which represents an application time interval of the radiation X until the upper limit for the dosage of the radiation X is reached. The radiation application time upper limit, as calculated by the radiation application time upper limit calculator 76, is supplied to the X-ray tube controller 68. When the period of time that has elapsed from initiation of application of the radiation X exceeds the radiation application time upper limit, the X-ray tube controller 68 outputs an interruption signal to the X-ray tube 66 in order to interrupt emission of the radiation X. The display panel 39 and a speaker 78, which jointly make up an announcing means, are connected to the X-ray tube controller 68. Based on the interruption signal generated by the X-ray tube controller 68, the display panel 39 displays an alarm message, whereas the speaker 78 produces an alarm sound, announcing that application of the radiation X has been interrupted.

The mammographic system 12 according to the present embodiment is basically constructed as described above. Operations of the mammographic system 12 shall be described below with reference to the flowchart shown in FIG. 5.

Figure 5:
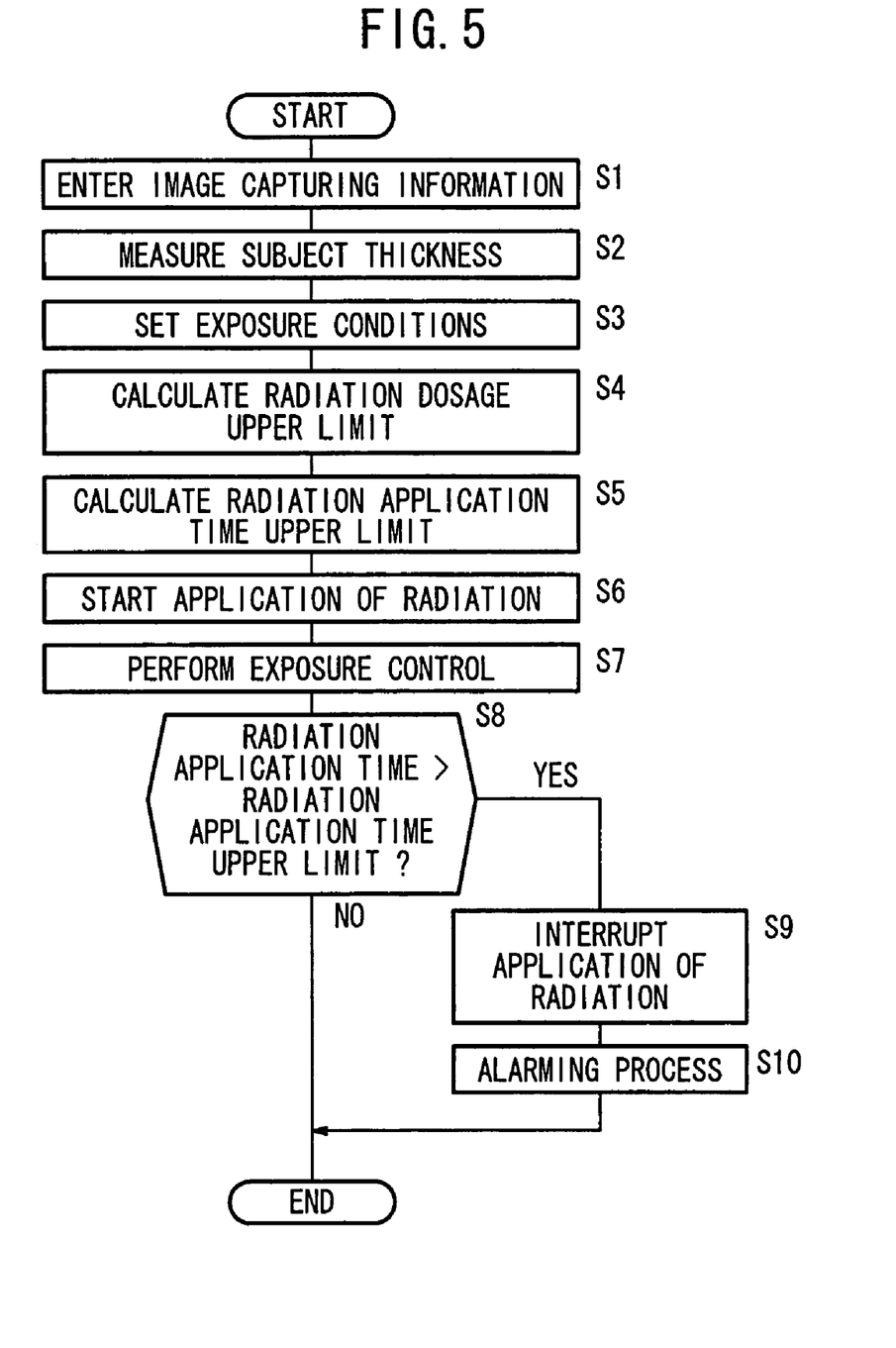
FIG. 5 is a flowchart of an operation sequence of the mammographic system according to the embodiment of the present invention.

Using the control panel 40 attached to the mammographic system 12, the non-illustrated console, and/or an ID card, etc., the operator enters image capturing information including ID information of the subject 32, an image capturing direction, an image capturing region, the tube voltage to be applied to the X-ray tube 66, the type of the target 54 of the X-ray tube 66, etc. (step S1). In the description that follows, it shall be assumed that the operator is capable of setting image capturing information using the control panel 40 and of confirming the image capturing information displayed on the display panel 39.

Thereafter, the operator places the mammographic system 12 into a certain state according to the specified image capturing direction. For example, the breast 44 may be imaged as a cranio-caudal view (CC) taken from above, a medio-lateral view (ML) taken outwardly from the center of the chest, or a medio-lateral oblique view (MLO) taken from an oblique view. Depending on the selected information of one of these image capturing directions, the operator turns the arm 30 about the swing shaft 28.

Then, the operator places the subject into a specified image capturing state with respect to the mammographic system 12. For example, if the breast 44 of the subject 32 is to be imaged as a cranio-caudal view (CC), the operator places the subject's breast 44 onto the image capturing base 36, and thereafter lowers the presser plate 38 to hold the breast 44 in place between the image capturing base 36 and the presser plate 38, as shown in FIG. 3.

After the breast 44 has been placed in a desired image capturing state, the subject thickness measuring unit 62 measures a subject thickness, i.e., the thickness of the breast 44 (step S2), and supplies the measured data to the exposure condition setting unit 64 and the radiation dosage upper limit calculator 74.

Using information of the region to be imaged of the subject 32 and the tube voltage, which have been entered from the control panel 40, the parameters read from the parameter memory 60, which include the absorption rate of the region to be imaged where the region to be imaged absorbs the radiation X, the absorption rates at which the filter, the presser plate 38, and the Bucky unit absorb the radiation X, the sensitivity of the X-ray detector 46, an index depending on the atomic number of the target 54, the attenuation characteristics of the radiation X depending on the distance between the target 54 and the X-ray detector 46, and the subject thickness supplied from the subject thickness measuring unit 62, the exposure condition setting unit 64 calculates a tube current to be supplied to the X-ray tube 66 along with a radiation application time, calculates the dosage of the radiation X that is required to capture a radiation image of the region to be imaged from the tube current and the radiation application time, and sets the calculated values as exposure conditions in the X-ray tube controller 68 (step S3).

For example, assuming the energy of the radiation X to be applied to the X-ray detector 46 is represented by E, the energy E is expressed by:

$$E = K \cdot V^n \cdot I \cdot t \cdot S/L^2 \cdot \exp(-\mu \cdot d) \tag{1}$$

where K represents a characteristic value peculiar to the mammographic system 12, V is the tube voltage, n is a tube voltage index, t is the application time of the radiation X, S is the sensitivity of the X-ray detector 46, L is the distance between the target 54 and the X-ray detector 46, $\mu$ is the absorption rate at which the region to be imaged absorbs the radiation X, and d is the subject thickness. If the energy E required in order for the X-ray detector 46 to be able to detect the radiation X is given highly accurately, then the tube current I and the radiation application time t, which are required to capture the radiation image, can be established according to the above equation (1), using the parameters including the subject thickness d. More strictly, for the calculation according to equation (1), it is necessary to take into account the absorption rates at which the Bucky unit and the air layer absorb the radiation X, as well as the thicknesses of the Bucky unit and the air layer. The required radiation dosage can be given as the product of the tube current I and the radiation application time t, which are used for obtaining the energy E.

The radiation dosage upper limit calculator 74 calculates the radiation dosage upper limit for the dosage of the radiation X that can be applied to the breast 44, using as a parameter the subject thickness d as measured by the subject thickness measuring unit 62 (step S4).

Since the subject 32 has its composition subject to individual differences, the radiation dosage upper limit can be established as a maximum radiation dosage capable of forming a problem-free image when the radiation image of the subject 32 is captured whose absorbed amount of radiation X is greatest.

Then, when the radiation X emitted with the tube current I set by the exposure condition setting unit 64 is applied to the breast 44 of the subject 32, the radiation application time upper limit calculator 76 calculates, as a radiation application time upper limit, the period of time consumed until the radiation dosage upper limit calculated in step S4 is reached (step S5). The calculated radiation application time upper limit is set in the X-ray tube controller 68.

After completing the above preparatory process, the X-ray tube controller 68 applies the tube voltage entered from the control panel 40 to the X-ray tube 66, and supplies the tube current set by the exposure condition setting unit 64 to the X-ray tube 66, thereby applying the radiation X to the breast 44 in order to start capturing a radiation image thereof (step S6).

Specifically, the X-ray tube controller 68 applies the tube voltage between the cathode 56 and the target 54 of the X-ray tube 66, and supplies the tube current therebetween, which is set as an exposure condition. The cathode 56 emits the electron beam "e", which bombards the target 54, thereby causing the target 54 to emit radiation X. The radiation X emitted from the target 54 passes through the opening 58 and is applied through the presser plate 38 to the breast 44. The radiation X passes through the breast 44 and is applied to the X-ray detector 46, which is housed in the image capturing base 36. Before a radiation image is captured, the entire surface of the X-ray detector 46 is irradiated with erasing light from the erasing light source 50 in order to remove unwanted electric charges from the X-ray detector 46. Thereafter, the X-ray detector 46 is placed in the two-dot-and-dash-line position as shown in FIG. 3.

After the radiation X has passed through the breast 44, the radiation X carries radiation image information of the breast 44. When the radiation X, which carries the radiation image information of the breast 44, is applied to the X-ray detector 46 while a high voltage is applied between the first electrically conductive layer and the second electrically conductive layer, pairs of positive and negative electric charges are generated in the recording photoconductive layer of the X-ray detector 46. The negative electric charges are stored in the electric energy storage region that is provided in the interface between the recording photoconductive layer and the charge transport layer. The amount of stored negative electric charges, i.e., the amount of latent image polarity electric charges, is substantially proportional to the dose of the radiation X that has passed through the breast 44. The positive electric charges generated within the recording photoconductive layer are attracted to the first electrically conductive layer, where they are combined with the negative electric charges of the applied high voltage and hence are eliminated.

A portion of the radiation X applied to the X-ray detector 46 passes through the X-ray detector 46 and is led to the exposure control sensor 47. The exposure control sensor 47 detects a radiation dosage of the radiation X and supplies the detected radiation dosage to the exposure controller 72. The exposure controller 72 integrates the detected radiation dosage, and then supplies the integrated radiation dosage back to the X-ray tube controller 68 through a feedback loop. The X-ray tube controller 68 controls application of the radiation X to the breast 44 according to the required radiation dosage, which is set as the exposure condition, and the integrated radiation dosage supplied from the exposure controller 72 (step S7).

Specifically, the X-ray tube controller 68 converts the radiation dosage supplied from the exposure controller 72 into a radiation dosage applied to the subject 32, and compares the converted radiation dosage with the required radiation dosage. When the compared radiation dosages agree with each other, the X-ray tube controller 68 controls the X-ray tube 66 to stop emitting radiation X. Consequently, the subject 32 is irradiated with an adequate amount of radiation X, in order to capture an appropriate radiation image thereof.

If the exposure control sensor 47 and/or the exposure controller 72 suffer from defects, then the X-ray tube 66 is not appropriately controlled by the signal from the exposure controller 72, and a larger amount of radiation X than required is applied to the X-ray detector 46, possibly resulting in a failure to capture an appropriate radiation image of the subject 32. Further, if an implant is embedded in the subject 32, then since the dose of radiation X that passes through the subject 32 is reduced, the radiation dosage applied to the subject 32 cannot properly be detected.

The X-ray tube controller 68 compares the radiation application time upper limit, as supplied from the radiation application time upper limit calculator 76, with the radiation application time, which represents the period of time that has elapsed from initiation of the application of the radiation X to the subject 32. If the radiation application time becomes greater than the radiation application time upper limit (YES in step S8), then the X-ray tube controller 68 outputs an interruption signal to the X-ray tube 66 for interrupting application of the radiation X to the subject 32 (step S9). Therefore, the X-ray detector 46 is prevented in advance from being irradiated with an excessive amount of radiation X, due to defects in the exposure control sensor 47 and/or the exposure controller 72, or due to an implant embedded in the subject 32.

Based on the interruption signal, the X-ray tube controller 68 controls the display panel 39 in order to display an alarm message indicating that application of the radiation X has been interrupted. The X-ray tube controller 68 also controls the speaker 78 in order to output an alarm sound, which also indicates that application of the radiation X has been interrupted (step S10). Such an alarm process notifies the operator that the radiation image capturing cycle has been interrupted.

When the cycle of capturing a radiation image by applying the radiation X according to the exposure conditions to the breast 44 is finished, the X-ray detector 46 is moved to a reading position, as indicated by the solid lines in FIG. 3. Then, the reading light source 48 moves in the direction indicated by the arrow along the X-ray detector 46 while applying the reading light to the X-ray detector 46. In the X-ray detector 46, pairs of positive and negative electric charges are generated within the reading photoconductive layer, and the positive electric charges are attracted to the negative electric charges (latent image polarity electric charges) stored in the electric energy storage region, and move within the charge transport layer. The positive electric charges then combine with the negative electric charges in the electric energy storage region and are eliminated. The negative electric charges generated within the reading photoconductive layer are combined with the negative electric charges supplied to the second photoelectric conductive layer and are eliminated. In this manner, the negative electric charges stored in the X-ray detector 46 are eliminated by charge combination, whereupon a current is developed within the X-ray detector 46 due to movement of the electric charges for performing charge combination. The current developed within the X-ray detector 46 is supplied to the radiation image forming unit 70, which produces a radiation image of the breast 44 based on the supplied current. After the radiation image has been formed, the X-ray detector 46 is irradiated with erasing light emitted from the erasing light source 50 in order to remove unwanted electric charges accumulated within the X-ray detector 46, and thereby preparing the X-ray detector 46 for the next radiation image capturing cycle.

A mammographic system according to another embodiment of the present invention shall be described below.

Figure 6:
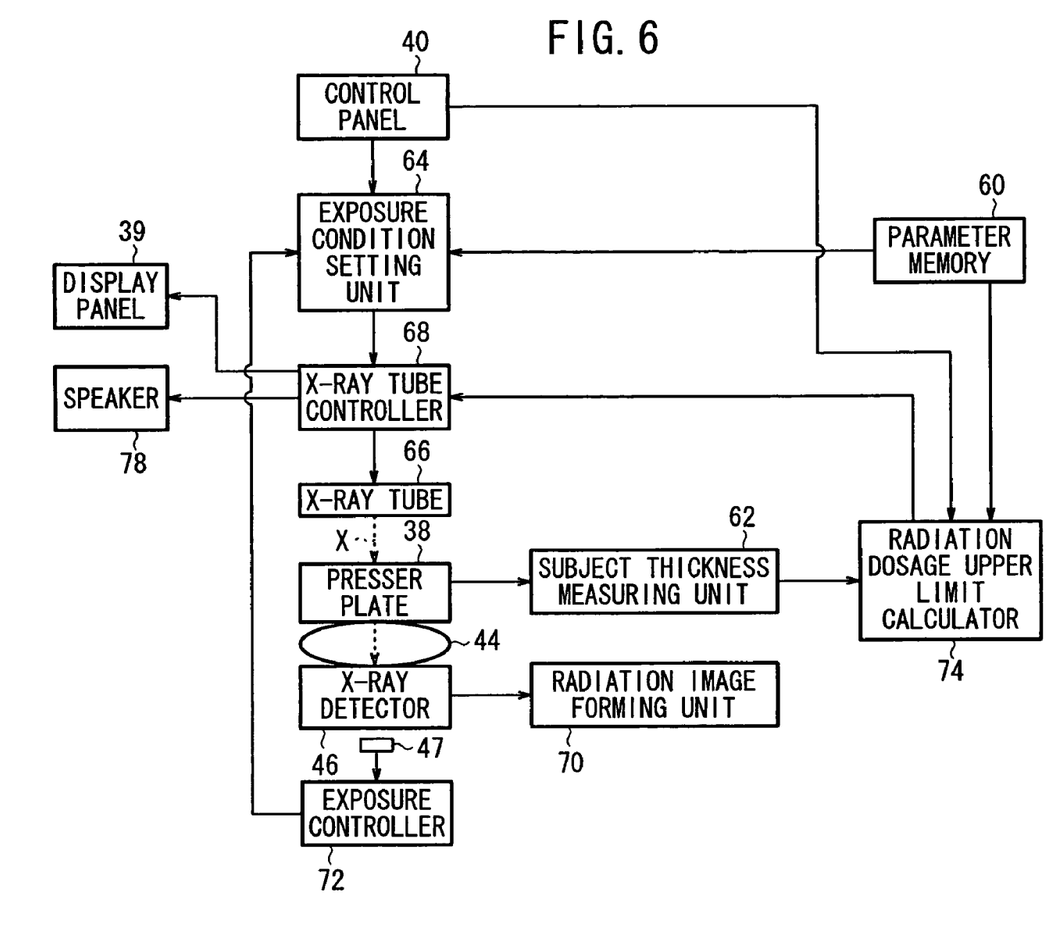
FIG. 6 is a block diagram of a control circuit of a mammographic system according to another embodiment of the present invention.

FIG. 6 shows in block form a control circuit of a mammographic system 12 according to another embodiment of the present invention. Those parts in FIG. 6, which are identical to those of the control circuit shown in FIG. 4, are denoted by identical reference numerals, and hence shall not be described in detail below. In the embodiment shown in FIG. 6, a required radiation dosage is calculated from the dosage of radiation X, which is detected by the exposure control sensor 47.

The subject 32 is set in the state shown in FIG. 3, and a prescribed dose of radiation X is applied to the subject 32 for a short period of time, while the dosage of radiation X that has passed through the subject 32 is detected by the exposure control sensor 47. The exposure controller 72 integrates the radiation dosage supplied from the exposure control sensor 47, and supplies the integrated radiation dosage to the exposure condition setting unit 64. The exposure condition setting unit 64 then calculates a required radiation dosage, based on the radiation dosage supplied from the exposure controller 72, and supplies the calculated required radiation dosage to the X-ray tube controller 68.

The radiation dosage upper limit calculator 74 calculates a radiation dosage upper limit, with respect to the dosage of the radiation X that can be applied to the breast 44, using as a parameter the subject thickness d as measured by the subject thickness measuring unit 62. The radiation dosage upper limit calculator 74 then supplies the calculated radiation dosage upper limit to the X-ray tube controller 68.

The X-ray tube controller 68 compares the required radiation dosage supplied from the exposure condition setting unit 64 with the radiation dosage upper limit supplied from the radiation dosage upper limit calculator 74. If the required radiation dosage is greater than the radiation dosage upper limit, the X-ray tube controller 68 outputs a cancellation signal to the X-ray tube 66 in order to cancel application of the radiation X in advance. When the X-ray tube 66 is controlled in this manner, application of the radiation X can be cancelled in advance, in the event that an inappropriate required radiation dosage is established due to defects of the exposure control sensor 47 and/or the exposure controller 72, or due to an implant embedded in the subject 32.

Based on the cancellation signal, the X-ray tube controller 68 controls the display panel 39 so as to display an alarm message, which indicates that application of the radiation X has been cancelled. The X-ray tube controller 68 also controls the speaker 78 so as to output an alarm sound, also indicating that application of the radiation X has been cancelled. The alarm message and the alarm sound allow the operator to recognize, before the radiation image is captured, that an inappropriate required radiation dosage is established and/or that a given device failure has occurred.

Instead of the X-ray detector 46, a radiation detecting means for converting the radiation X that has passed through the breast 44 directly into an electric signal may be employed. Based on the dosage of radiation X detected by such a radiation detecting means, the X-ray tube controller 68 may be controlled, or a required radiation dosage may be established.

Although certain preferred embodiments of the present invention have been shown and described in detail, it should be understood that various changes and modifications may be made to the embodiments without departing from the scope of the invention set forth in the appended claims.

What is claimed is:

1. An apparatus for capturing a radiation image by emitting radiation from a radiation source and applying the radiation to a subject, comprising:
   required dosage setting means for setting a required radiation dosage required to capture the radiation image;
   radiation dosage upper limit setting means for setting a radiation dosage upper limit for the radiation applied to said subject;
   radiation application time upper limit setting means for setting a radiation application time upper limit until said radiation dosage upper limit is reached;
   radiation dosage detecting means for detecting a radiation dosage of said radiation applied to said subject; and
   radiation source control means for controlling said radiation source based on the radiation dosage of said radiation detected by said radiation dosage detecting means to apply the required radiation dosage of said radiation to said subject, monitoring a radiation application time in which said radiation is applied to said subject, and interrupting application of said radiation to said subject if the radiation application time exceeds said radiation application time upper limit.

2. An apparatus according to claim 1, wherein said radiation dosage upper limit setting means sets said radiation dosage upper limit based on image capturing information with respect to a region to be imaged of said subject.

3. An apparatus according to claim 1, wherein said radiation dosage upper limit setting means sets said radiation dosage upper limit based on image capturing information with respect to a thickness of a region to be imaged of said subject along a direction in which said radiation passes through said subject.

4. An apparatus according to claim 1, wherein said apparatus comprises a mammographic system.

5. An apparatus according to claim 1, further comprising:
   announcing means for announcing that said radiation source control means has controlled said radiation source to interrupt application of said radiation to said subject.

6. An apparatus according to claim 1, wherein said radiation dosage upper limit setting means sets said radiation dosage upper limit based on positional information of the subject.

7. An apparatus according to claim 1, wherein the radiation application time upper limit is determined based on the radiation dosage upper limit set by the radiation dosage upper limit setting means.

8. An apparatus according to claim 6, wherein the positional information of the subject is based on a thickness of the subject determined using a presser plate which presses and holds the subject against a base.

9. An apparatus according to claim 1, wherein the radiation application time upper limit is calculated based on the radiation dosage upper limit.

10. An apparatus for capturing a radiation image by emitting radiation from a radiation source and applying the radiation to a subject, comprising:
   radiation dosage upper limit setting means for setting a radiation dosage upper limit for the radiation applied to said subject, wherein the radiation dosage upper limit is based on information of a subject thickness;
   radiation dosage detecting means for detecting a radiation dosage of said radiation applied to said subject;
   required dosage setting means for setting a required radiation dosage required to capture the radiation image, based on said radiation dosage detected by said radiation dosage detecting means; and radiation source control means for controlling said radiation source based on the radiation dosage of said radiation detected by said radiation dosage detecting means to apply the required radiation dosage of said radiation to said subject, and canceling application of said radiation to said subject if said required radiation dosage exceeds said radiation dosage upper limit.

11. An apparatus according to claim 10, wherein said radiation dosage upper limit setting means sets said radiation dosage upper limit based on image capturing information with respect to a region to be imaged of said subject.

12. An apparatus according to claim 10, wherein said radiation dosage upper limit setting means sets said radiation dosage upper limit based on image capturing information with respect to a thickness of a region to be imaged of said subject along a direction in which said radiation passes through said subject.

13. An apparatus according to claim 10, wherein said apparatus comprises a mammographic system.

14. An apparatus according to claim 10, further comprising:
announcing means for announcing that said radiation source control means has controlled said radiation source to cancel application of said radiation to said subject.

15. An apparatus according to claim 10, wherein the positional information of the subject is based on a thickness of the subject determined using a presser plate which presses and holds the subject against a base.

16. An apparatus according to claim 10, wherein the positional information of the subject is based on a thickness of the subject determined using a presser plate which presses and holds the subject against a base.

17. An apparatus according to claim 13, wherein the information of a subject thickness is acquired based on positional information of a presser plate.

18. A method of capturing a radiation image by emitting radiation from a radiation source and applying the radiation to a subject, comprising the steps of:
setting a required radiation dosage required to capture the radiation image;
setting a radiation dosage upper limit for the radiation applied to said subject;
setting a radiation application time upper limit until said radiation dosage upper limit is reached;
detecting a radiation dosage of said radiation applied to said subject;
controlling said radiation source based on the radiation dosage of said radiation and applying the required radiation dosage of said radiation to said subject to capture the radiation image; and
monitoring a radiation application time in which said radiation is applied to said subject and interrupting application of said radiation to said subject if the radiation application time exceeds said radiation application time upper limit.

19. A method according to claim 18, further comprising the step of:
announcing an interrupted state when application of said radiation to said subject is interrupted.

20. A method according to claim 18, wherein the setting a radiation dosage upper limit is based on positional information of the subject.

21. A method according to claim 18, wherein the radiation application time upper limit is determined based on the radiation dosage upper limit set by the radiation dosage upper limit setting means.

22. A method according to claim 20, wherein the positional information of the subject is based on a thickness of the subject determined using a presser plate which presses and holds the subject against a base.

23. A method according to claim 18, wherein the radiation application time upper limit is calculated based on the radiation dosage upper limit.

24. A method of capturing a radiation image by emitting radiation from a radiation source and applying the radiation to a subject, comprising the steps of:
setting a radiation dosage upper limit for the radiation applied to said subject, wherein the radiation dosage upper limit is based on information of a subject thickness;
detecting a radiation dosage of said radiation applied to said subject;
setting a required radiation dosage required to capture the radiation image, based on said radiation dosage;
controlling said radiation source to cancel application of said radiation to said subject if said required radiation dosage exceeds said radiation dosage upper limit; and
controlling said radiation source to apply the required radiation dosage of said radiation to said subject to capture a radiation image thereof, if said required radiation dosage does not exceed said radiation dosage upper limit.

25. A method according to claim 24, further comprising the step of:
announcing a cancelled state when application of the radiation to said subject is cancelled.

26. A method according to claim 24, wherein said step of setting a required radiation dosage further comprises the step of:
applying a dose of said radiation to said subject in an amount which is smaller than when said radiation image is captured.

27. A method according to claim 24, wherein the positional information of the subject is based on a thickness of the subject determined using a presser plate which presses and holds the subject against a base.

* * * * *